United States Patent
Kumar et al.

(10) Patent No.: US 11,034,629 B1
(45) Date of Patent: Jun. 15, 2021

(54) INTEGRATED PERCHLOROETHYLENE DECOMPOSITION REACTOR DESIGN FOR C4 AND C5-6 ISOMERIZATION UNITS

(71) Applicant: UOP LLC, Des Plaines, IL (US)

(72) Inventors: Manoj Kumar, Haryana (IN); David J. Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/734,471

(22) Filed: Jan. 6, 2020

(51) Int. Cl.
*C07C 5/27* (2006.01)
*C07C 7/11* (2006.01)

(52) U.S. Cl.
CPC .............. *C07C 5/2791* (2013.01); *C07C 7/11* (2013.01); *C07C 2523/42* (2013.01); *C07C 2523/44* (2013.01); *C07C 2523/755* (2013.01)

(58) Field of Classification Search
None
See application file for complete search history.

(56) References Cited

U.S. PATENT DOCUMENTS

| | | | | |
|---|---|---|---|---|
| 2,454,149 | A * | 11/1948 | Franklin | C07C 9/12 585/736 |
| 10,479,741 | B2 | 11/2019 | Kumar et al. | |
| 2013/0074870 | A1* | 3/2013 | Norton | C10G 45/62 134/3 |
| 2015/0175506 | A1 | 6/2015 | Shakur | |
| 2016/0107954 | A1* | 4/2016 | Pigourier | C10G 45/60 585/748 |

FOREIGN PATENT DOCUMENTS

| CN | 108079988 A | 5/2018 |
|---|---|---|
| WO | 0032544 | 6/2000 |

OTHER PUBLICATIONS

U.S. Appl. No. 16/263,733, filed Jan. 31, 2019 entitled "Processes and Apparatus for Isomerizing Hydrocarbons".
International Search Report from PCT/US2021/012134 dated Apr. 8, 2021.
Written Opinion from PCT/US2021/012134 dated Apr. 8, 2021.

\* cited by examiner

*Primary Examiner* — Philip Y Louie
*Assistant Examiner* — Alyssa L Cepluch

(57) ABSTRACT

Processes incorporating a common organic chloride decomposition reactor and chloride treater to be used by both the $C_4$ and $C_{5-6}$ isomerization reaction zones are described. A portion of the $C_4$ isomerization reaction zone off gas is routed to the $C_4$ HCl absorber, which provides about 85% of the HCl requirement for the $C_4$ isomerization reaction zone. A small amount of the $C_{5-6}$ isomerization reaction zone off gas is mixed with the $C_4$ isomerization reaction zone off gas portion going to the $C_4$ HCl absorber.

20 Claims, 1 Drawing Sheet

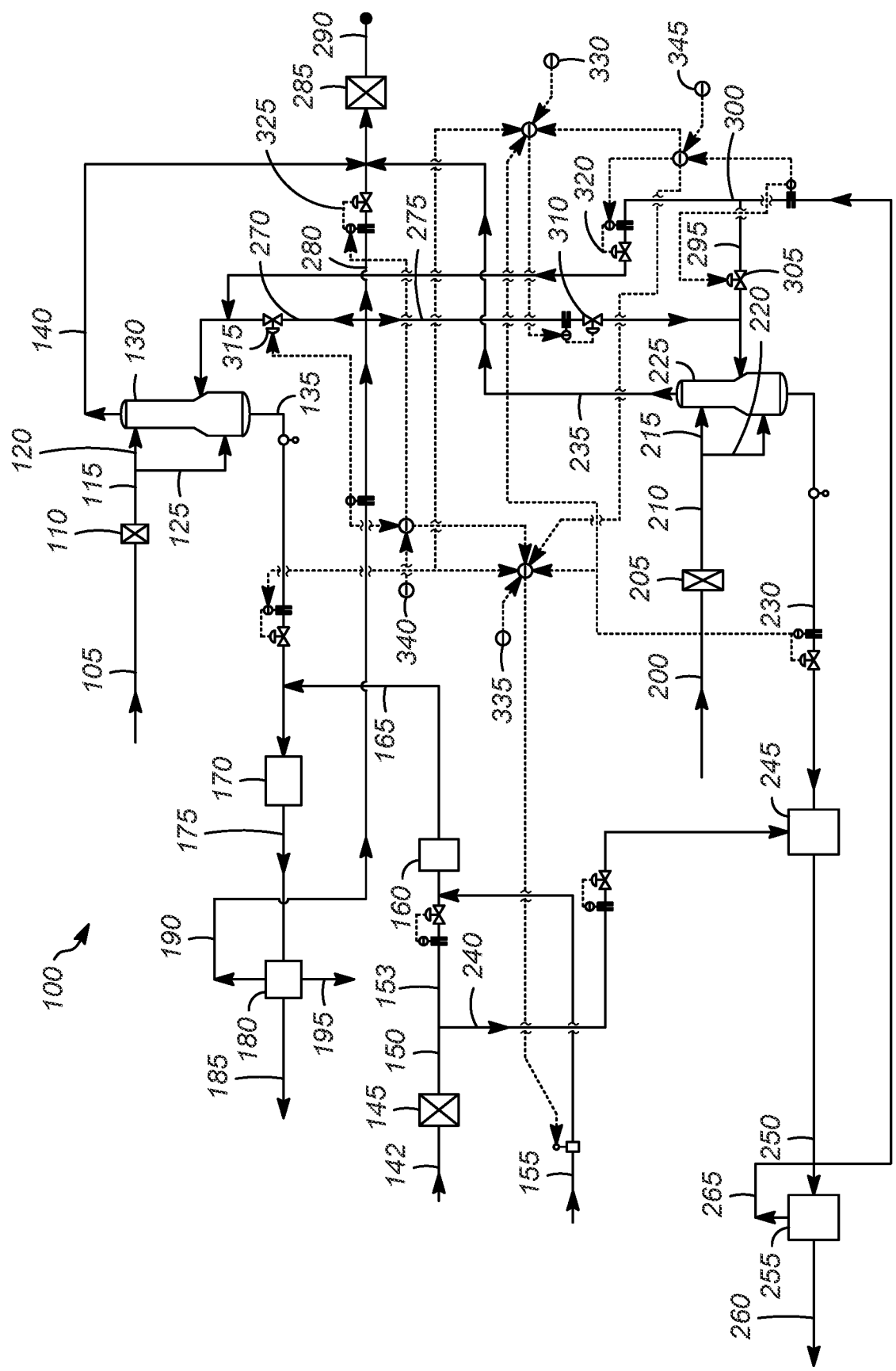

INTEGRATED PERCHLOROETHYLENE DECOMPOSITION REACTOR DESIGN FOR C4 AND C5-6 ISOMERIZATION UNITS

BACKGROUND OF THE INVENTION

Isomerization processes are widely used by many refiners to rearrange the molecular structure of straight chain paraffinic hydrocarbons to more highly branched hydrocarbons that generally have higher octane ratings. Many isomerization processes employ a chlorinated catalyst, such as chlorinated alumina catalyst, chlorinated platinum aluminum catalyst, and the like, in a reaction zone (e.g., refers to an area including one or more reactors). The chlorinated catalyst requires a continuous addition of chloride to replace chloride removed from the surface of the catalyst and carried away in the reaction-zone effluent. Typically, a fresh feed of chloride promoter, such as perchloroethylene, is continuously introduced into a paraffin feed stream upstream from a reactor in the reaction zone. Inside the reactor, the chloride promoter decomposes to form hydrogen chloride that activates, e.g., promotes or regenerates, the catalyst by replenishing the chloride removed from the catalyst's surface. The UOP PENEX™ processes developed by UOP LLC, Des Plaines, Ill. typically employ two or more fixed-bed reactors situated in a lead-lag configuration. The reactors contain chlorided platinum-alumina catalyst, which is contacted with a light straight-run (LSR) naphtha feed, hydrogen gas, and a trace organic chloride injection, all of which have been dried to ensure that water (a catalyst poison and corrosion enabler) is not introduced into the process. The organic chloride is converted to hydrogen chloride (HCl), which promotes and maintains the high activity of the catalyst, while the hydrogen serves to aid the product selectivity toward branched isomers by suppressing the polymerization of olefinic intermediates.

Many isomerization units use a chloride source such as perchloroethylene (PERC) to provide the required HCl to the chlorided alumina catalyst to ensure optimal isomerization function. The decomposition temperature of perchloroethylene in the isomerization reaction zone constrains the isomerization reaction zone to a higher temperature than is optimal for the isomerization function. Because the minimum decomposition temperature of perchloroethylene to HCl is 105° C., the typical minimum inlet temperature for C4 and C5-C6 isomerization reaction zones has been 105° C.

Processes have been developed in which HCl from the isomerization reactor effluent stream is recovered in an HCl absorber and recycled back to the reactor zone. This reduces the net organic chloride injection rate by 80-90% making the process more efficient. These processes are described in U.S. Pat. No. 10,479,741, and U.S. application Ser. No. 16/263,733, filed Jan. 31, 2019, entitled "PROCESSES AND APPARATUS FOR ISOMERIZING HYDROCARBONS", each of which is incorporated herein by reference in its entirety.

Processes have also been developed in which a separate reactor is provided for the decomposition of the organic chloride. The product of the decomposition of the organic chloride is sent to the isomerization reaction zone along with a hydrocarbon feed containing paraffins. The use of the organic chloride decomposition reactor allows the operating temperatures for the isomerization reaction zone to be reduced. These processes are described in U.S. application Ser. No. 16/412,108, filed May 14, 2019, entitled PERCHLOROETHYLENE DECOMPOSITION REACTOR DESIGN FOR ISOMERIZATION UNIT HYDROGEN FEED, ENABLING A LOWER TEMPERATURE PROCESS WITH INCREASED C5+ YIELD, and U.S. application Ser. No. 16/368,461, filed Mar. 28, 2019, entitled INTEGRATION OF AN ORGANIC CHLORIDE DECOMPOSITION REACTOR ON THE ISOMERIZATION/DEISOBUTANIZER C5 DRAG STREAM, each of which is incorporated herein by reference in its entirety.

Some gasoline complexes have both $C_4$ and $C_{5-6}$ isomerization units. $C_4$ isomerization units produce feed for alkylation units which produce alkylate for gasoline blending. $C_{5-6}$ isomerization units produce isomerate which is sent to gasoline blending. Providing each isomerization unit with its own chloride decomposition and gas treatment units unnecessarily increases the expense of the overall process.

Therefore, there is a need for improved isomerization processes in which the $C_4$ and $C_{5-6}$ isomerization units use the same chloride decomposition unit and gas treatment unit.

Definitions

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, $C_2$, $C_3$ . . . $C_n$ where "n" represents the number of carbon atoms in the hydrocarbon molecule. In addition, the term "$C_n$-$C_{n+1}$ hydrocarbon," such as "$C_5$-$C_6$ hydrocarbon," can mean at least one of a $C_5$ or $C_6$ hydrocarbon.

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor, drier or vessel, can further include one or more zones or sub-zones. It should be understood that each zone can include more equipment and/or vessels than depicted in the drawing.

As used herein, the term "fluid transfer device" generally means a device for transporting a fluid. Such devices include pumps typically for liquids, and compressors typically for gases.

As used herein, the term "rich" can mean an amount generally of at least about 50%, and preferably about 70%, by mole, of a compound or class of compounds in a stream.

As used herein, the term "substantially" can mean an amount generally of at least about 90%, preferably about 95%, and optimally about 99%, by mole, of a compound or class of compounds in a stream.

As used herein, the term "about" means within plus or minus 10% of the specified value, or within plus or minus 5%, or within plus or minus 1%.

BRIEF DESCRIPTION OF THE DRAWING

The FIGURE is an illustration of one embodiment of an isomerization process according to the present invention.

DETAILED DESCRIPTION

The present invention provides a common organic chloride decomposition reactor and chloride treater to be used by both the $C_4$ and $C_{5-6}$ isomerization reaction zones. It improves overall chloride recovery from 85% to more than 92%. Moreover, the use of the common chloride decomposition reactor and chloride treater decreases the equipment costs for the process, as well as reducing the amount of chloride treater adsorbent by around 50%. Because the adsorbent quantity has gone down significantly, and the gas flow rate has gone up due to the presence of the combined off gas for $C_4$ and $C_{5-6}$ isomerization reaction zones, the use of a net gas compressor can be avoided, which results in addition capital savings. In addition, the process allows the elimination of chloride injection to the $C_4$ isomerization reaction zone.

A portion of the $C_4$ isomerization reaction zone off gas, typically about 85%, will be routed to the $C_4$ HCl absorber. The rest of the gas (about 15%) will go to the $C_{5-6}$ HCl absorber, along with the $C_{5-6}$ isomerization reaction zone off gas portion, instead of going to the chloride treater. This provides about 85% of the HCl requirement for the $C_4$ isomerization reaction zone. A small portion of the $C_{5-6}$ isomerization reaction zone off gas (e.g., about 8% for the case selected) is mixed with the $C_4$ isomerization reaction zone off gas portion going to the $C_4$ HCl absorber. Thus, the $C_4$ isomerization reaction zone's HCl requirement can be met without fresh injection of organic chloride to the $C_4$ isomerization reaction zone. The amount of $C_{5-6}$ isomerization reaction zone off gas to be routed to the $C_4$ HCl absorber can be calculated based on the $C_4$ feed rate, the ratio of $C_4$ off gas sent to the $C_4$ HCl absorber to the total amount of $C_4$ off gas, and the $C_{5-6}$ feed rate. The amount of $C_{5-6}$ isomerization reaction zone off gas (ratio) sent to the $C_4$ HCl absorber (i.e., the second $C_{5-6}$ off gas stream) equals:

$$A^*(1-B^*D)/C$$

where A is the $C_4$ feed rate; B is the ratio of the first $C_4$ off gas stream sent to the $C_4$ HCl absorber to a total amount of the $C_4$ off gas stream; C is the $C_{5-6}$ feed rate; and D is the fraction of HCl recovered from the combination of the first $C_4$ off gas stream and the second $C_{5-6}$ off gas stream sent to the $C_4$ HCl absorber.

The $C_4$ isomerization reaction zone off gas purge (e.g., about 15%) sent to the $C_{5-6}$ isomerization reaction zone will not result in the accumulation of light ends because the $C_{5-6}$ HCl absorber operates at lower pressure than the $C_4$ stabilizer column so there is less absorption of $C_1$-$C_3$ hydrocarbons. The $C_3$ hydrocarbons in the $C_4$ isomerization reaction zone off gas absorbed in the $C_{5-6}$ HCl absorber will be rejected in the $C_{5-6}$ isomerization reaction zone's liquefied petroleum gas (LPG) stream.

A portion of the $C_{5-6}$ isomerization reaction zone off gas is routed directly to the chloride treater as a purge stream to avoid accumulation of light ends in the system. For a standalone $C_{5-6}$ isomerization reaction zone with a chloride decomposition reactor, typically about 15% of the total $C_{5-6}$ isomerization reaction zone off gas is purged to avoid accumulation. However, in this case, about 8% of $C_{5-6}$ isomerization unit off gas is already routed to the $C_4$ HCl absorber. Therefore, a 10% purge of the $C_{5-6}$ isomerization reaction zone off gas is sufficient, as it makes the total $C_{5-6}$ isomerization reaction zone off gas purge about 18%. Depending on the purity of the makeup gas and other parameters, the $C_{5-6}$ isomerization reaction zone off gas purge could be reduced from about 10% to about 5%, further increasing the overall HCl recovery.

The remaining portion of the $C_{5-6}$ isomerization reaction zone off gas, about 82% in this case, is routed to the $C_{5-6}$ HCl absorber. The remaining portion of the $C_{5-6}$ isomerization reaction zone HCl requirement is met by injecting organic chloride to the $C_{5-6}$ isomerization reaction zone through the organic chloride decomposition reactor.

The chloride equivalent of the remaining portion of the $C_{5-6}$ isomerization reaction zone HCl requirement, i.e., the amount of chloride equivalent in the chloride effluent stream equals:

$$C^*G^*(1-E^*F)-A^*G^*(1-B)^*F$$

where: A is the $C_4$ feed rate; B is the ratio of the amount of the first $C_4$ off gas stream sent to the $C_4$ HCl absorber to the total amount of the $C_4$ off gas stream; C is the $C_{5-6}$ feed rate; E is the ratio of an amount of the first $C_{5-6}$ off gas stream to the total amount of the $C_{5-6}$ off gas stream; F is the fraction of HCl recovered from the combination of the first $C_{5-6}$ off gas stream and the second $C_4$ off gas stream sent to the $C_{5-6}$ HCl absorber; and G is a constant which depends on process parameters and the type of chloriding agent used.

G is determined by the desired chloride injection rate divided by the fraction equivalent of chloride in the chloriding agent. For example, when the organic chloride comprises perchloro ethylene and where there is a requirement of 150 wppm Cl in the isomerization reaction zone) G equals 150/0.855. For carbon tetrachloride and an injection rate of 150 wppm, G equals 150/0.898.

The integrated process allows more than about 92% recovery of HCl from the $C_4$ and $C_{5-6}$ isomerization reaction zone off gases versus about 85% for typical individual units. This reduces the net HCl in the combined off gases sent to the chloride treater for treatment by around 50%. This not only decreases the amount of chloride adsorbent by about 50%, but it also avoids the use of an off gas compressor, which would otherwise be required to achieve a minimum velocity for efficient adsorption. This results in a significant reduction in the capital and operating expense for the process.

Integration allows reasonable amount of purges from the system to avoid any accumulation of light ends.

The integrated process for $C_4$ isomerization and $C_{5-6}$ isomerization starts by passing a portion of $C_{5-6}$ feed stream to a $C_{5-6}$ HCl absorber while the remainder goes to a bottoms surge bypassing the trays. The $C_{5-6}$ feed stream comprises normal pentane and normal hexane, and in some cases, some heptanes. A portion of the $C_{5-6}$ isomerization off gas stream comprising $H_2$, $C_1$-$C_4$ and HCl is fed to the $C_{5-6}$ HCl absorber. The $C_{5-6}$ HCl absorber is operated a temperature of about 37.8° C. to about 48.9° C. (about 100° F. to about 120° F.) and a pressure of about 1.1 MPa(g) to about 1.6 MPa(g) (about 160 psig to about 225 psig). The $C_{5-6}$ HCl absorber bottoms stream comprising normal pentane, normal hexane, and HCL is routed to the $C_{5-6}$ isomerization reaction zone. The $C_{5-6}$ HCl absorber overhead stream has a trace amount of HCl (e.g., less than about 10) along with hydrogen, $C_1$-$C_2$ hydrocarbons and some $C_3$-$C_4$ hydrocarbons. It is mixed with a portion of the $C_{5-6}$ HCl off gas stream and the $C_4$ HCl absorber overhead stream before routing to the chloride treater for further treatment.

A hydrogen rich gas stream and a chloride feed stream containing an organic chloride compound are sent to an organic chloride decomposition reactor. The organic chloride decomposition reactor contains a chloride decomposition catalyst to decompose the organic chloride compound forming a chloride effluent stream comprising hydrogen, hydrocarbon, and HCl. The hydrogen to organic chloride molar ratio in the organic chloride decomposition reactor is typically about 350:1 to about 2700:1. The chloride decomposition catalyst typically comprises at least one of: nickel, platinum, or palladium. The organic chloride compound typically comprises one or more of a perchloro $C_1$-$C_4$ hydrocarbon or carbon tetrachloride.

The $C_{5-6}$ absorber bottoms stream and the chloride effluent stream are sent to a $C_{5-6}$ isomerization reaction zone containing a $C_{5-6}$ isomerization catalyst. The $C_{5-6}$ feed stream reacts under $C_{5-6}$ isomerization conditions to convert a portion of the normal pentane and normal hexane to iso-pentane and iso-hexane. The $C_{5-6}$ isomerization effluent formed comprises normal pentane, normal hexane, iso-pentane, iso-hexane, and gases. Suitable $C_{5-6}$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 0.5 to about 12 $hr^{-1}$.

The $C_{5-6}$ isomerization effluent is sent to a $C_{5-6}$ stabilizer column where it is separated into at least a $C_{5-6}$ product stream comprising the normal pentane, normal hexane, iso-pentane, and iso-hexane, and a $C_{5-6}$ off gas stream. The $C_{5-6}$ off gas stream typically comprises hydrogen, $C_{1-2}$ hydrocarbons, and HCl, along with some $C_{3-4}$ hydrocarbons. In some embodiments, there is also a liquefied petroleum gas (LPG) stream comprising $C_{3-4}$ hydrocarbons.

A portion of a $C_4$ feed stream is passed to a $C_4$ HCl absorber, and the remainder goes to a bottoms surge bypassing the trays. The $C_4$ feed stream mainly comprises normal butane, and in some cases, some propane and some $C_5$ hydrocarbons. A portion of the $C_4$ isomerization off gas stream comprising $H_2$, $C_1$-$C_3$ hydrocarbons, and HCl is fed to the $C_4$ HCl absorber. The $C_4$ HCl absorber is operated a temperature of about 37.8° C. to about 48.9° C. (about 100° F. to about 120° F.) and a pressure of about 1.1 MPa(g) to about 1.6 MPa(g) (about 160 psig to about 225 psig). The $C_4$ absorber bottoms stream comprises butanes and HCL, and it is routed to the $C_4$ isomerization reaction zone. The $C_4$ HCl absorber overhead stream has a trace amount of HCl (e.g., less than about 10 ppm vol) along with hydrogen, $C_1$-$C_2$ hydrocarbons and some $C_3$-$C_4$ hydrocarbons. It is mixed with the $C_{5-6}$ HCl absorber overhead stream along with a portion of the $C_{5-6}$ HCl absorber off gas stream and routed to the chloride treater to remove the remaining amount of HCl from the combined off gas stream.

The $C_4$ absorber bottoms stream is sent to a $C_4$ isomerization reaction zone containing a $C_4$ isomerization catalyst and operating under $C_4$ isomerization conditions where a portion of the normal butane is converted to iso-butane. Typical $C_4$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 4 to about 24 $hr^{-1}$. The $C_4$ isomerization effluent comprises normal butane, iso-butane, and gases.

The $C_4$ isomerization effluent is separated in a $C_4$ stabilizer column into at least a $C_4$ product stream comprising the normal butane, and iso-butane, and a $C_4$ off gas stream. The $C_4$ off gas stream typically comprises hydrogen, $C_{1-2}$ hydrocarbons, some $C_3$ hydrocarbons, and HCl.

The $C_{5-6}$ off gas stream is split into three streams. The first $C_{5-6}$ off gas stream is sent to the $C_{5-6}$ HCl absorber. The second $C_{5-6}$ off gas stream is sent to the $C_4$ HCl absorber. The third $C_{5-6}$ off gas stream is sent to the chloride treater. Typically, the first $C_{5-6}$ off gas stream comprises about 75 to about 90% of the $C_{5-6}$ off gas stream, the second $C_{5-6}$ off gas stream comprises about 5 to about 15% of the $C_{5-6}$ off gas stream, and the third $C_{5-6}$ off gas stream comprises about 5 to about 20% of the $C_{5-6}$ off gas stream.

The $C_4$ off gas stream is split into two streams. The first $C_4$ off gas stream is sent to the $C_4$ HCl absorber, and the second $C_4$ off gas stream is sent to the $C_{5-6}$ HCl absorber. Typically, the first $C_4$ off gas stream comprises about 75 to about 95% of the $C_4$ off gas stream, and the second $C_4$ off gas stream comprises about 5 to about 25% of the $C_4$ off gas stream.

The $C_{5-6}$ absorber overhead stream from the $C_{5-6}$ HCl absorber and the $C_4$ absorber overhead stream from the $C_4$ HCl absorber are combined with the third $C_{5-6}$ off gas stream and sent to the chloride treater.

The amount of HCl required in the $C_4$ absorber bottoms stream is determined, and the flow rate of the second $C_{5-6}$ off gas stream to the $C_4$ HCl absorber is controlled based on that amount.

The separation of the $C_{5-6}$ isomerization effluent in the $C_{5-6}$ stabilizer column may include separating the $C_{5-6}$ isomerization effluent into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms. The last stream may also contain about 2% hydrocarbons having 2 carbon atoms and about 2% hydrocarbons having 5 carbon atoms.

The $C_{5-6}$ product stream can be sent to a deisohexanizer column, and the $C_4$ product stream can be sent to a deisobutanizer column.

The $C_{5-6}$ feed stream may be dried before it is sent to the $C_{5-6}$ HCl absorber. The $C_4$ feed stream may be dried before it is sent to the $C_4$ HCl absorber.

The amount of the second $C_{5-6}$ off gas stream sent to the $C_4$ HCl absorber may be calculated using the equation:

$$A*(1-B*D)/C$$

where: A is the $C_4$ feed rate; B is the ratio of the amount of the first $C_4$ off gas stream sent to the $C_4$ HCl absorber to the total amount of the $C_4$ off gas stream; C is the $C_{5-6}$ feed rate; and D is the fraction of HCl recovered from the combination of the first $C_4$ off gas stream and the second $C_{5-6}$ off gas stream sent to the $C_4$ HCl absorber.

The organic chloride compound may comprise one or more of: perchloro $C_1$-$C_4$ hydrocarbon or carbon tetrachloride. The amount of chloride equivalent in the chloride effluent stream can be calculated using the equation:

$$C*G*(1-E*F)-A*G*(1-B)*F$$

where: A is a $C_4$ feed rate; B is a ratio of an amount of the first $C_4$ off gas stream sent to the $C_4$ HCl absorber (i.e., the first $C_4$ off gas stream 295) to a total amount of $C_4$ off gas (i.e., $C_4$ off gas stream 265); C is the $C_{5-6}$ feed rate; E is the ratio of the amount of the first $C_{5-6}$ off gas stream (i.e. the first $C_{5-6}$ off gas stream 270) to the total amount of the $C_{5-6}$ off gas stream (i.e. $C_{5-6}$ off gas stream 190); F is the fraction of HCl recovered from the combination of the first $C_{5-6}$ off gas stream (i.e. the first $C_{5-6}$ off gas stream 270) and the second $C_4$ off gas stream (i.e. the second $C_4$ off gas stream 300) sent to the $C_{5-6}$ HCl absorber; and G is a constant which depends on process parameters and the type of chloriding agent used.

D is the fraction of HCl recovered from the off gas entering the $C_4$ HCl absorber (i.e., the combination of the first $C_4$ off gas stream and the second $C_{5-6}$ off gas stream). The amount in each stream can be determined by an HCl analyzer or by laboratory analysis. For example, one way to determine this is to have a sample station and flow measurement, either direct or indirect, on the $C_4$ off gas stream entering the $C_4$ HCl absorber, on the $C_{5-6}$ off gas stream entering the $C_4$ HCl absorber and on the $C_4$ overhead stream. D is the amount of HCl in the off gases entering the $C_4$ HCl absorber minus the amount of HCl in the $C_4$ overhead stream divided by the amount of HCl in the off gases entering the $C_4$ HCl absorber. For example, if the combination of the first $C_4$ off gas stream and the second $C_{5-6}$ off gas stream entering the $C_4$ HCl absorber contained 100 lbs of HCl and the $C_4$ overhead stream contained 0.1 lbs of HCl, D would be (100-0.1)/100=0.999.

F is the fraction of HCl recovered from the off gases entering the $C_{5-6}$ HCl absorber (i.e., the combination of the first $C_{5-6}$ off gas stream and the second $C_4$ off gas stream). The amount in each stream can be determined by an HCl analyzer or by laboratory analysis. For example, one way to determine this is to have a sample station and flow measurement, either direct or indirect, on the $C_{5-6}$ off gas stream entering the $C_{5-6}$ HCl absorber, on the C4 off gas stream entering the C5-6 HCl absorber and on the $C_{5-6}$ overhead stream. F is the amount of HCl in the off gases entering the $C_{5-6}$ HCl absorber minus the amount of HCl in the $C_{5-6}$ overhead stream divided by the amount of HCl in the off gases entering the $C_{5-6}$ HCl absorber. The calculation of F is similar to that for D described above.

One aspect of the invention is an integrated process for $C_4$ isomerization and $C_{5-6}$ isomerization. In one embodiment, the process comprises: passing a $C_{5-6}$ feed stream comprising normal pentane and normal hexane to a $C_{5-6}$ HCl absorber forming a $C_{5-6}$ HCl absorber bottoms stream comprising normal pentane, normal hexane and HCL, and a $C_{5-6}$ overhead stream comprising a trace amount of HCl; passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl; passing the $C_{5-6}$ HCl absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane forming a $C_{5-6}$ isomerization effluent comprising normal pentane, normal hexane, iso-pentane, iso-hexane, and gases; separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream; passing a $C_4$ feed stream comprising normal butane to a $C_4$ HCl absorber forming a $C_4$ HCl absorber bottoms stream comprising normal butane and HCL, and a $C_4$ overhead stream comprising a trace amount of HCl; passing the $C_4$ HCl absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases; separating the $C_4$ isomerization effluent in a $C_4$ stabilizer column into at least a $C_4$ product stream comprising the normal butane, iso-butane, and a $C_4$ off gas stream; splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises about 75 to about 90% of the $C_{5-6}$ off gas stream, the second $C_{5-6}$ off gas stream comprises about 5 to about 15% of the $C_{5-6}$ off gas stream, and the third $C_{5-6}$ off gas stream comprises about 5 to about 20% of the $C_{5-6}$ off gas stream; splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises about 75 to about 95% of the $C_4$ off gas stream, and the second $C_4$ off gas stream comprises about 5 to about 25% of the $C_4$ off gas stream; passing the $C_{5-6}$ absorber overhead stream from the $C_{5-6}$ absorber and the $C_4$ absorber overhead stream from the $C_4$ HCl absorber to the chloride treaters In some embodiments, the process further comprises: determining an amount of HCl required in the $C_4$ HCl absorber bottoms stream; and controlling a flow rate of the second portion of $C_{5-6}$ off gas stream to the $C_4$ HCl absorber.

In some embodiments, separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms.

In some embodiments, the process further comprises at least one of: passing the $C_{5-6}$ product stream to a deisohexanizer column; or passing the $C_4$ product stream to a deisobutanizer column.

In some embodiments, the process further comprises at least one of: drying the $C_{5-6}$ feed stream before passing the $C_{5-6}$ feed stream to the $C_{5-6}$ HCl absorber; or drying the $C_4$ feed stream before passing the $C_4$ feed stream to the $C_4$ HCl absorber.

In some embodiments, at least one of: the $C_{5-6}$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 0.5 to about 12 $hr^{-1}$; or the $C_4$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 4 to about 24 $hr^{-1}$.

In some embodiments, the hydrogen to organic chloride molar ratio in the organic chloride decomposition reactor is about 350:1 to about 2700:1.

In some embodiments, the chloride decomposition catalyst comprises at least one of: nickel, platinum, or palladium.

In some embodiments, the organic chloride compound comprises one or more of a perchloro $C_1$-$C_4$ hydrocarbon or carbon tetrachloride.

In some embodiments, the amount of chloride equivalent in the chloride effluent stream can be calculated using the equation:

$$C*G*(1-E*F)-A*G*(1-B)*F$$

where: A is a $C_4$ feed rate; B is a ratio of an amount of the first $C_4$ off gas stream sent to the $C_4$ HCl absorber (i.e., the first $C_4$ off gas stream 295) to a total amount of the $C_4$ off gas stream (i.e., the $C_4$ off gas stream 265); C is the $C_{5-6}$ feed rate; E is the ratio of the amount of the first $C_{5-6}$ off gas stream to the total amount of the $C_{5-6}$ off gas stream; F is the fraction of HCl recovered from the combination of the first $C_{5-6}$ off gas stream and the second $C_4$ off gas stream sent to the $C_{5-6}$ HCl absorber; and G is a constant which depends on process parameters and the type of chloriding agent used.

In some embodiments, the amount of the second $C_{5-6}$ off gas stream sent to the $C_4$ HCl absorber (i.e., the second $C_{5-6}$ off gas stream 275) can be calculated using the equation:

$$A*(1-B*D)/C$$

where: A is a $C_4$ feed rate; B is a ratio of the amount of the first $C_4$ off gas stream sent to the $C_4$ HCl absorber (i.e., the first $C_4$ off gas stream 295) to the total amount of the $C_4$ off gas stream (i.e., the $C_4$ off gas stream 265); C is a $C_{5-6}$ feed rate; and D is the fraction of HCl recovered from the off combination of the first $C_4$ gas stream and the second $C_{5-6}$ off gas stream sent to the $C_4$ HCl absorber.

Another aspect of the invention is an integrated process for $C_4$ isomerization and $C_{5-6}$ isomerization. In one embodiment, the process comprises: passing a $C_{5-6}$ feed stream comprising normal pentane and normal hexane to a $C_{5-6}$ HCl absorber forming a $C_{5-6}$ absorber bottoms stream comprising normal pentane, normal hexane and HCL and a $C_{5-6}$ absorber overhead stream comprising a trace amount of HCl; passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl; passing the $C_{5-6}$ absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane forming a $C_{5-6}$ isomerization effluent comprising normal pentane, normal hexane, iso-pentane, iso-hexane, and gases; separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream; passing a $C_4$ feed stream comprising normal butane to a $C_4$ HCl absorber forming a $C_4$ absorber bottoms stream comprising normal butane and HCL and a $C_4$ overhead stream comprising a trace amount of HCl; passing the $C_4$ absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases; separating the $C_4$ isomerization effluent in a $C_4$ stabilizer column into at least a $C_4$ product stream comprising the normal butane, iso-butane, and a $C_4$ off gas stream; splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises 75 to 90% of the $C_{5-6}$ off gas stream, the second $C_{5-6}$ off gas stream comprises 5 to 15% of the $C_{5-6}$ off gas stream, and the third $C_{5-6}$ off gas stream comprises 5 to 20% of the $C_{5-6}$ off gas stream; splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises 75 to 95% of the $C_4$ off gas stream, and the second $C_4$ off gas stream comprises 5 to 25% of the $C_4$ off gas stream; passing the $C_{5-6}$ HCl absorber overhead stream from the $C_{5-6}$ HCl absorber and the $C_4$ absorber overhead stream from the $C_4$ HCl absorber to the chloride treaters; passing the $C_{5-6}$ product stream to a deisohexanizer column; and passing the $C_4$ product stream to a deisobutanizer column.

In some embodiments, the process further comprises: determining an amount of HCl required in the $C_4$ HCl absorber bottoms stream; and controlling a flow rate of the second $C_{5-6}$ off gas stream to the $C_4$ HCl absorber.

In some embodiments, separating the $C_{5-6}$ isomerization effluent in the $C_{5-6}$ stabilizer column into at least the $C_{5-6}$ product stream comprising the normal pentane, normal hexane, iso-pentane, and iso-hexane, and the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms.

In some embodiments, the process further comprises at least one of: drying the first feed stream before passing the $C_{5-6}$ feed stream to the $C_{5-6}$ HCl absorber; or drying the $C_4$ feed stream before passing the $C_4$ feed stream to the $C_4$ HCl absorber.

In some embodiments, at least one of: the $C_{5-6}$ isomerization conditions comprise one or more of: a temperature in a range of 80° C. to 215° C.; a pressure in a range of 1.4 MPa(g) to 7.0 MPa(g); or a liquid hourly space velocity in a range of 0.5 to 12 $hr^{-1}$; or the $C_4$ isomerization conditions comprise one or more of: a temperature in a range of 80° C. to 215° C.; a pressure in a range of 1.4 MPa(g) to 7.0 MPa(g); or a liquid hourly space velocity in a range of 4 to 24 $hr^{-1}$.

In some embodiments, the hydrogen to organic chloride molar ratio in the organic chloride decomposition reactor is 350:1 to 2700:1.

In some embodiments, the chloride decomposition catalyst comprises at least one of: nickel, platinum, or palladium.

In some embodiments, the organic chloride compound comprises one or more of a perchloro $C_1$-$C_4$ hydrocarbon or carbon tetrachloride, and the amount of chloride equivalent in the chloride effluent stream can be calculated using the equation:

$$C*G*(1-E*F)-A*G*(1-B)*F$$

where: A is the $C_4$ feed rate; B is the ratio of the amount of the first $C_4$ off gas stream sent to the $C_4$ HCl absorber to a total amount of the $C_4$ off gas stream; C is a $C_{5-6}$ feed rate; E is a ratio of the first $C_{5-6}$ off gas stream to the total amount of the $C_{5-6}$ off gas stream; F is a fraction of HCl recovered from the combination of the first $C_{5-6}$ off gas stream and the second $C_4$ off gas stream sent to the $C_{5-6}$ HCl absorber; and G is a constant which depends on process parameters and the type of chloriding agent used.

In some embodiments, the amount of the second $C_{5-6}$ off gas stream can be calculated using an equation:

$$A*(1-B*D)/C$$

where: A is a $C_4$ feed rate; B is a ratio of the amount of the first $C_4$ off gas stream sent to the $C_4$ HCl absorber to the total amount of the $C_4$ off gas stream; C is a $C_{5-6}$ feed rate; and D is the fraction of HCl recovered from the combination of the first $C_4$ off gas stream and the second $C_{5-6}$ off gas stream sent to the $C_4$ HCl absorber.

The FIGURE illustrates one embodiment of the integrated process 100 for $C_4$ isomerization and $C_{5-6}$ isomerization of the present invention.

The $C_{5-6}$ feed stream 105 comprising normal pentane and normal hexane with some heptane is sent to a drier 110. The dried $C_{5-6}$ feed stream 115 is split into dried $C_{5-6}$ feed stream 120 and dried $C_{5-6}$ feed stream 125 which are sent to the $C_{5-6}$ HCl absorber 130 which produces a $C_{5-6}$ absorber bottoms stream 135 and a $C_{5-6}$ absorber overhead stream 140 comprising $H_2$, $C_{1-4}$ and a trace amount of HCl.

A hydrogen rich gas stream 142 is sent to drier 145. The dried hydrogen rich gas stream 150 is split into two streams.

Stream 153 is combined with a chloride feed stream 155 containing an organic chloride compound and sent to the chloride decomposition reactor 160. The chloride decomposition reactor 160 contains a chloride decomposition catalyst which decomposes the organic chloride compound into HCl. The chloride decomposition catalyst comprises at least one of: nickel, platinum, or palladium. The hydrogen to organic chloride molar ratio in the organic chloride decomposition reactor is typically about 350:1 to about 2700:1. Suitable organic chloride compound include, but are not limited to, one or more of a perchloro $C_1$-$C_4$ hydrocarbons or carbon tetrachloride. The chloride effluent stream 165 comprises hydrogen, hydrocarbons, and HCl.

The chloride equivalent of chloride feed stream 155 equals:

$$C*G*(1-E*F)-A*G*(1-B)*F$$

where: A is a $C_4$ feed rate; B is the ratio of the first $C_4$ off gas stream sent to the $C_4$ HCl absorber to a total amount of the $C_4$ off gas stream; C is a $C_{5-6}$ feed rate; E is a ratio of the amount of the first $C_{5-6}$ off gas stream sent to the total amount of the $C_{5-6}$ off gas stream; F is the fraction of HCl recovered from the combination of the first $C_{5-6}$ off gas stream and the second $C_4$ off gas stream sent to the $C_{5-6}$ HCl absorber; and G is a constant which depends on process parameters and the type of chloriding agent used.

The $C_{5-6}$ absorber bottoms stream 135 and chloride effluent stream 165 are sent to the $C_{5-6}$ isomerization reaction zone 170. The $C_{5-6}$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 0.5 to about 12 $hr^{-1}$. The $C_{5-6}$ isomerization catalyst comprises a chlorinated catalyst. A portion of the normal pentane and normal hexane is converted to iso-pentane and iso-hexane.

The $C_{5-6}$ isomerization effluent 175, which comprises normal pentane, normal hexane, iso-pentane, and iso-hexane, is sent to the $C_{5-6}$ stabilizer column 180. It is separated into at least $C_{5-6}$ product stream 185, and a $C_{5-6}$ off gas stream 190. The $C_{5-6}$ product stream 185 comprises normal pentane, normal hexane, iso-pentane, and iso-hexane. The $C_{5-6}$ off gas stream 190 comprises hydrogen, $C_{1-2}$ hydrocarbons, HCl, and in some cases some $C_{3-4}$ hydrocarbons. Optionally, there may be a LPG product stream 195.

The $C_4$ feed stream 200 comprising normal butane is sent to a drier 205. The dried $C_4$ feed stream 210 is split into dried $C_4$ feed stream 215 and dried $C_4$ feed stream 220 which are sent to the $C_4$ HCl absorber 225 which produces a $C_4$ absorber bottoms stream 230 and a $C_4$ overhead stream 235 comprising a trace amount of HCl, along with hydrogen, $C_1$-$C_2$ hydrocarbons and some $C_3$-$C_4$ hydrocarbons.

The $C_4$ absorber bottoms stream 230 and a portion 240 of the dried hydrogen rich gas stream 150 are sent to the $C_4$ isomerization reaction zone 245. The $C_4$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 4 to about 24 $hr^{-1}$. The $C_4$ isomerization catalyst comprises a chlorided alumina catalyst containing Pt, for example. A portion of the normal butane is converted to iso-butane.

The $C_4$ isomerization effluent 250, which comprises normal butane, and iso-butane, is sent to the $C_4$ stabilizer column 255. It is separated into at least $C_4$ product stream 260, and a $C_4$ off gas stream 265. The $C_4$ product stream 260 comprises normal butane, and iso-butane. The $C_4$ off gas stream 265 comprises hydrogen, $C_{1-2}$ hydrocarbons, HCl, and in some cases some $C_3$ hydrocarbons.

The $C_{5-6}$ off gas stream 190 is split into three streams. The first $C_{5-6}$ off gas stream 270 is sent to the $C_{5-6}$ HCl absorber 130. The second $C_{5-6}$ off gas stream 275 is sent to the $C_4$ HCl absorber 225. The third $C_{5-6}$ off gas stream 280 is sent to the chloride treaters 285 where the chloride is removed. The treated off-gas stream 290 is typically sent to the fuel gas header of the refinery.

The first $C_{5-6}$ off gas stream 270 comprises about 75 to about 90% of the $C_{5-6}$ off gas stream 190; the second $C_{5-6}$ off gas stream 275 comprises about 5 to about 15% of the $C_{5-6}$ off gas stream 190; and the third $C_{5-6}$ off gas stream 280 comprises about 5 to about 20% of the $C_{5-6}$ off gas stream 190.

The $C_4$ off gas stream 265 is split into two streams. The first $C_4$ off gas stream 295 is sent to the $C_4$ HCl absorber 225, and the second $C_4$ off gas stream 300 is sent to the $C_{5-6}$ HCl absorber 130.

The first $C_4$ off gas stream 295 comprises about 75 to about 90% of the $C_4$ off gas stream 265; and the second $C_4$ off gas stream 300 comprises about 5 to about 15% of the $C_{5-6}$ off gas stream 265.

330 is the manual (DCS) input distributed control system of the recovery of HCl in the $C_4$ HCl absorber (i.e., D) based on laboratory analysis.

335 is the manual DCS input of the recovery of HCl in the $C_{5-6}$ HCl absorber (i.e., F) based on laboratory analysis.

340 is the manual DCS input for the ratio of The first $C_{5-6}$ off gas stream 270 to the $C_{5-6}$ off gas stream 190.

345 is the manual DCS input for the ratio of the first $C_4$ off gas stream 295 to the $C_4$ off gas stream 265.

The integration of the $C_4$ and $C_{5-6}$ isomerization HCL recovery sections allows for the control of the first $C_4$ off gas stream and the second $C_{5-6}$ off gas streams 295 and 275 sent to the $C_4$ HCl absorber 225 to allow it to produce a $C_4$ bottoms stream 230 that contains all of the HCL necessary for the $C_4$ isomerization reaction zone 245 without the addition of chloride. The only chloride addition required for the combined system during normal operation is a small makeup up to the $C_{5-6}$ isomerization reaction zone 170 from the organic chloride decomposition reactor 160. This is achieved by first measuring the unit feed rates for the $C_4$ and $C_{5-6}$ isomerization reaction zones 170 and 245 and calculating the amount of HCL required for each isomerization reaction zone 170 and 245 based on the specification of e.g., 150 wt ppm chloride in the liquid feed to the isomerization reaction zones 170 and 245. Since the HCL fed to the isomerization reaction zones 170 and 245 is not consumed, all the HCl from the isomerization reaction zones 170 and 245 ends up in the $C_{5-6}$ and $C_4$ stabilizer off-gas streams 190 and 265. The $C_{5-6}$ and $C_4$ HCl absorbers 130 and 225 are designed to absorb approximately 99.5% of the HCl in the gas sent to the HCl absorber into the liquid that exists the absorber bottom. By controlling the flowrates of the first $C_4$ off gas stream 295 and the second $C_{5-6}$ off gas stream 275 sent to the $C_4$ HCl absorber using flow controllers 305 and 310 respectively, and the flowrates of the first $C_{5-6}$ off gas stream 270 and the second $C_4$ off gas stream 300 sent to the $C_{5-6}$ HCl absorber using flow controllers 315 and 320 respectively, the quantity of HCl in the $C_{5-6}$ and $C_4$ absorber bottoms streams 135 and 230 sent to the $C_{5-6}$ and $C_4$ isomerization reaction zones 170 and 245 can be controlled. The HCl absorption efficiency of 99.5% can be confirmed via laboratory analysis and actual values can be entered into the calculation blocks 330 and 335. The second $C_{5-6}$ stream 275 flow sent to the $C_4$ HCl absorber 225 is controlled by flow controller 310 to achieve a $C_4$ absorber bottoms stream 230 that contains all of the HCl necessary for the $C_4$ isomerization reaction zone 245. To prevent build-up of light ends in the system, a small quantity of the off gas streams i.e., the third $C_{5-6}$ off gas stream 280 controlled by flow controller 325, along with $C_{5-6}$ absorber overhead stream 140 and the $C_4$ absorber overhead stream 235, must be purged from the system and sent to chloride treaters 285. This small loss of HCl from the system is made up via the organic chloride sent to the chloride decomposition reactor 160 and from there in the chloride effluent stream 155 to the $C_{5-6}$ isomerization reaction zone 170.

The amount of organic chloride needed to be sent to the organic chloride decomposition reactor 160 can be calculated and controlled based on the amount of Cl required for each of the $C_4$ and $C_{5-6}$ isomerization reaction zones 245 and 170 as mentioned above and on the first $C_{5-6}$ off gas stream 270 and second $C_4$ off gas stream 300 rates sent to the $C_{5-6}$ HCl absorber 130. This can be done by adjusting the stroke of the injection pump (not shown).

The $C_{5-6}$ absorber overhead stream 140 from the $C_{5-6}$ HCl absorber 130 and the $C_4$ absorber overhead stream 235 from the $C_4$ HCl absorber 225 are combined with the third $C_{5-6}$ off gas stream 280 and sent to the chloride treaters 285.

Any of the above conduits, unit devices, scaffolding, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for $C_4$ isomerization and $C_{5-6}$ isomerization comprising passing a $C_{5-6}$ feed stream comprising normal pentane and normal hexane to a $C_{5-6}$ HCl absorber forming a $C_{5-6}$ absorber bottoms stream comprising normal pentane, normal hexane and HCL, and a $C_{5-6}$ absorber overhead stream comprising a trace amount of HCl; passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl; passing the $C_{5-6}$ absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane forming a $C_{5-6}$ isomerization effluent comprising normal pentane, normal hexane, iso-pentane, iso-hexane, and gases; separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream; passing a $C_4$ feed stream comprising normal butane to a $C_4$ HCl absorber forming a $C_4$ absorber bottoms stream comprising normal butane and HCL, and a $C_4$ absorber overhead stream comprising a trace amount of HCl; passing the $C_4$ absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases; separating the $C_4$ isomerization effluent in a $C_4$ stabilizer column into at least a $C_4$ product stream comprising the normal butane, iso-butane, and a $C_4$ off gas stream; splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises about 75 to about 90% of the $C_{5-6}$ off gas stream, the second $C_{5-6}$ off gas stream comprises about 5 to about 15% of the $C_{5-6}$ off gas stream, and the third $C_{5-6}$ off gas stream comprises about 5 to about 20% of the $C_{5-6}$ off gas stream; splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises about 75 to about 95% of the $C_4$ off gas stream, and the second $C_4$ off gas stream comprises about 5 to about 25% of the $C_4$ off gas stream; passing the $C_{5-6}$ absorber overhead stream from the $C_{5-6}$ HCl absorber and the $C_4$ absorber overhead stream from the $C_4$ HCl absorber to the chloride treaters. An embodiment of the invention is one, any or all of prior embodiments in this paragraph up through the first embodiment in this paragraph further comprising determining an amount of HCl required in the $C_4$ HCl absorber bottoms stream; and controlling a flow rate of the second $C_{5-6}$ off gas stream to the $C_4$ HCl absorber based on the determined amount of HCl required in the $C_4$ HCl absorber bottoms stream. An embodiment of the invention is one, any or all of prior embodiments in this paragraph up through the first embodiment in this paragraph wherein separating the $C_{5-6}$ isomerization effluent in the $C_{5-6}$ stabilizer column into at least the $C_{5-6}$ product stream comprising the normal pentane, normal hexane, iso-pentane, and iso-hexane, and the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms. An embodiment of the invention is one, any or all of prior embodiments in this paragraph up through the first embodiment in this paragraph further comprising at least one of passing the $C_{5-6}$ product stream to a deisohexanizer column; or passing the $C_4$ product stream to a deisobutanizer column. An embodiment of the invention is one, any or all of prior embodiments in this paragraph up through the first embodiment in this paragraph further comprising at least one of drying the $C_{5-6}$ feed stream before passing the $C_{5-6}$ feed stream to the $C_{5-6}$ HCl absorber; or drying the $C_4$ feed stream before passing the $C_4$ feed stream to the $C_4$ HCl absorber. An embodiment of the invention is one, any or all of prior embodiments in this paragraph up through the first embodiment in this paragraph wherein at least one of the $C_{5-6}$ isomerization conditions comprise one or more of a temperature in a range of about 80° C. to about 215° C.; a pressure in a range of about 1.4 MPa(g) to about 7.0 MPa(g); or a liquid hourly space velocity in a range of about 0.5 to about 12 hr¹; or the $C_4$ isomerization conditions comprise one or more of a temperature in a range of about 80° C. to about 215° C.; a pressure in a range of about 1.4 MPa(g) to about 7.0 MPa(g); or a liquid hourly space velocity in a range of about 4 to about 24 $hr^{-1}$. An embodiment of the invention is one, any or all of prior embodiments in this paragraph up through the first embodiment in this paragraph wherein a hydrogen to organic chloride molar ratio in the organic chloride decomposition reactor is about 350:1 to about 2700:1. An embodiment of the invention is one, any or all of prior embodiments in this paragraph up through the first embodiment in this paragraph wherein the chloride decomposition catalyst comprises at least one of nickel, platinum, or palladium. An embodiment of the invention is one, any or all of prior embodiments in this paragraph up through the first embodiment in this paragraph wherein the organic chloride compound comprises one or more of a perchloro $C_1$-$C_4$ hydrocarbon or carbon tetrachloride. An embodiment of the invention is one, any or all of prior embodiments in this paragraph up through the first embodiment in this paragraph wherein an amount of chloride equivalent in the chloride effluent stream can be calculated using an equation $C*G*(1-E*F)-A*G*(1-B)*F$ where A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; E is a ratio of an amount of the first $C_{5-6}$ off gas stream to the total amount of the $C_{5-6}$ off gas stream; F is a fraction of HCl recovered from a combination of the first $C_{5-6}$ off gas stream and the second $C_4$ off gas stream sent to the $C_{5-6}$ HCl absorber; and G is a constant which depends on process parameters and the type of chloriding agent used. An embodiment of the invention is one, any or all of prior embodiments in this paragraph up through the first embodiment in this paragraph wherein an amount of the second $C_{5-6}$ off gas stream can be calculated using an equation $A*(1-B*D)/C$ where A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; and D is a fraction of HCl recovered from a combination of the first $C_4$ off gas stream and the second $C_{5-6}$ off gas stream sent to the $C_4$ HCl absorber.

A second embodiment of the invention is a process for $C_4$ isomerization and $C_{5-6}$ isomerization comprising passing a $C_{5-6}$ feed stream comprising normal pentane and normal hexane to a $C_{5-6}$ HCl absorber forming a $C_{5-6}$ absorber bottoms stream comprising normal pentane, normal hexane and HCL and a $C_{5-6}$ absorber overhead stream comprising a trace amount of HCl; passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl; passing the $C_{5-6}$ absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane forming a $C_{5-6}$ isomerization effluent comprising normal pentane, normal hexane, iso-pentane, iso-hexane, and gases; separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream; passing a $C_4$ feed stream comprising normal butane to a $C_4$ HCl absorber forming a $C_4$ absorber bottoms stream comprising normal butane and HCl and a $C_4$ absorber overhead stream comprising a trace amount of HCl; passing the $C_4$ absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases; separating the $C_4$ isomerization effluent in a $C_4$ stabilizer column into at least a $C_4$ product stream comprising normal butane and iso-butane, and a $C_4$ off gas stream; splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises 75 to 90% of the $C_{5-6}$ off gas stream, the second $C_{5-6}$ off gas stream comprises 5 to 15% of the $C_{5-6}$ off gas stream, and the third $C_{5-6}$ off gas stream comprises 5 to 20% of the $C_{5-6}$ off gas stream; splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises 75 to 95% of the $C_4$ off gas stream, and the second $C_4$ off gas stream comprises 5 to 25% of the $C_4$ off gas stream; passing the $C_{5-6}$ absorber overhead stream from the $C_{5-6}$ HCl absorber and the $C_4$ absorber overhead stream from the $C_4$ HCl absorber to the chloride treaters; passing the $C_{5-6}$ product stream to a deisohexanizer column; and passing the $C_4$ product stream to a deisobutanizer column. An embodiment of the invention is one, any or all of prior embodiments in this paragraph up through the second embodiment in this paragraph further comprising determining an amount of HCl required in the $C_4$ absorber bottoms stream; and controlling a flow rate of the second $C_{5-6}$ off gas stream to the $C_4$ HCl absorber based on the determined amount of HCl required in the $C_4$ HCl absorber bottoms stream. An embodiment of the invention is one, any or all of prior embodiments in this paragraph up through the second embodiment in this paragraph wherein separating the $C_{5-6}$ isomerization effluent in the $C_{5-6}$ stabilizer column into at least the $C_{5-6}$ product stream comprising the normal pentane, normal hexane, iso-pentane, and iso-hexane, and the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms. An embodiment of the invention is one, any or all of prior embodiments in this paragraph up through the second embodiment in this paragraph further comprising at least one of drying the first feed stream before passing the $C_{5-6}$ feed stream to the $C_{5-6}$ HCl absorber; or drying the $C_4$ feed stream before passing the $C_4$ feed stream to the $C_4$ HCl absorber. An embodiment of the invention is one, any or all of prior embodiments in this paragraph up through the second embodiment in this paragraph wherein at least one of the $C_{5-6}$ isomerization conditions comprise one or more of a temperature in a range of about 80° C. to about 215° C.; a pressure in a range of about 1.4 MPa(g) to about 7.0 MPa(g); or a liquid hourly space velocity in a range of about 0.5 to about 12 hr'; or the $C_4$ isomerization conditions comprise one or more of a temperature in a range of about 80° C. to about 215° C.; a pressure in a range of about 1.4 MPa(g) to about 7.0 MPa(g); or a liquid hourly space velocity in a range of about 4 to about 24 $hr^{-1}$. An embodiment of the invention is one, any or all of prior embodiments in this paragraph up through the second embodiment in this paragraph wherein a hydrogen to organic chloride molar ratio in the organic chloride decomposition reactor is about 350; 1 to about 2700:1. An embodiment of the invention is one, any or all of prior embodiments in this paragraph up through the second embodiment in this paragraph wherein the chloride decomposition catalyst comprises at least one of nickel, platinum, or palladium. An embodiment of the invention is one, any or all of prior embodiments in this paragraph up through the second embodiment in this paragraph wherein an amount of chloride equivalent in the chloride effluent stream can be calculated using an equation C*G*(1−E*F)−A*G*(1−B)*F where A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; E is a ratio of an amount of the first $C_{5-6}$ off gas stream to the total amount of the $C_{5-6}$ off gas stream; F is a fraction of HCl recovered from a combination of the first $C_{5-6}$ off gas stream and the second $C_4$ off gas stream sent to the $C_{5-6}$ HCl absorber; and G is a constant which depends on process parameters and the type of chloriding agent used. An embodiment of the invention is one, any or all of prior embodiments in this paragraph up through the second embodiment in this paragraph wherein an amount of the second $C_{5-6}$ stream can be calculated using an equation A*(1−B*D)/C where A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; and D is a fraction of HCl recovered from a combination of the first $C_4$ off gas stream and the second $C_{5-6}$ off gas stream sent to the $C_4$ HCl absorber.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. An integrated process for $C_4$ isomerization and $C_{5-6}$ isomerization comprising:

passing a $C_{5-6}$ feed stream comprising normal pentane and normal hexane to a $C_{5-6}$ HCl absorber forming a $C_{5-6}$ absorber bottoms stream comprising normal pentane, normal hexane and HCl, and a $C_{5-6}$ absorber overhead stream comprising a trace amount of HCl;

passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl;

passing the $C_{5-6}$ absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane, forming a $C_{5-6}$ isomerization effluent comprising normal pentane, normal hexane, iso-pentane, iso-hexane, and gases;

separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream;

passing a $C_4$ feed stream comprising normal butane to a $C_4$ HCl absorber forming a $C_4$ absorber bottoms stream comprising normal butane and HCl, and a $C_4$ absorber overhead stream comprising a trace amount of HCl;

passing the $C_4$ absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases;

separating the $C_4$ isomerization effluent in a $C_4$ stabilizer column into at least a $C_4$ product stream comprising the normal butane and iso-butane, and a $C_4$ off gas stream;

splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises about 75 to about 90% of the $C_{5-6}$ off gas stream, the second $C_{5-6}$ off gas stream comprises about 5 to about 15% of the $C_{5-6}$ off gas stream, and the third $C_{5-6}$ off gas stream comprises about 5 to about 20% of the $C_{5-6}$ off gas stream;

splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises about 75 to about 95% of the $C_4$ off gas stream, and the second $C_4$ off gas stream comprises about 5 to about 25% of the $C_4$ off gas stream; and passing the $C_{5-6}$ absorber overhead stream from the $C_{5-6}$ HCl absorber and the $C_4$ absorber overhead stream from the $C_4$ HCl absorber to the chloride treaters.

2. The process of claim 1 further comprising:

determining an amount of HCl required in the $C_4$ HCl absorber bottoms stream; and controlling a flow rate of the second $C_{5-6}$ off gas stream to the $C_4$ HCl absorber based on the determined amount of HCl required in the $C_4$ HCl absorber bottoms stream.

3. The process of claim 1 wherein separating the $C_{5-6}$ isomerization effluent in the $C_{5-6}$ stabilizer column into at least the $C_{5-6}$ product stream comprising the normal pentane, normal hexane, iso-pentane, and iso-hexane, and the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms.

4. The process of claim 1 further comprising at least one of:
passing the $C_{5-6}$ product stream to a deisohexanizer column; or
passing the $C_4$ product stream to a deisobutanizer column.

5. The process of claim 1 further comprising at least one of:
drying the $C_{5-6}$ feed stream before passing the $C_{5-6}$ feed stream to the $C_{5-6}$ HCl absorber; or
drying the $C_4$ feed stream before passing the $C_4$ feed stream to the $C_4$ HCl absorber.

6. The process of claim 1 wherein at least one of: the $C_{5-6}$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 0.5 to about 12 $hr^{-1}$; or the $C_4$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 4 to about 24 $hr^{-1}$.

7. The process of claim 1 wherein a hydrogen to organic chloride molar ratio in the organic chloride decomposition reactor is about 350:1 to about 2700:1.

8. The process of claim 1 wherein the chloride decomposition catalyst comprises at least one of: nickel, platinum, or palladium.

9. The process of claim 1 wherein the organic chloride compound comprises one or more of a perchloro $C_1$-$C_4$ hydrocarbon or carbon tetrachloride.

10. The process of claim 9 wherein an amount of chloride equivalent in the chloride effluent stream can be calculated using an equation:

$$C*G*(1-E*F)-A*G*(1-B)*F$$

where: A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; E is a ratio of an amount of the first $C_{5-6}$ off gas stream to the total amount of the $C_{5-6}$ off gas stream; F is a fraction of HCl recovered from a combination of the first $C_{5-6}$ off gas stream and the second $C_4$ off gas stream sent to the $C_{5-6}$ HCl absorber; and G is a constant which depends on process parameters and the type of chloriding agent used.

11. The process of claim 1 wherein an amount of the second $C_{5-6}$ off gas stream can be calculated using an equation:

$$A*(1-B*D)/C$$

where: A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; and D is a fraction of HCl recovered from a combination of the first $C_4$ off gas stream and the second $C_{5-6}$ off gas stream sent to the $C_4$ HCl absorber.

12. An integrated process for $C_4$ isomerization and $C_{5-6}$ isomerization comprising:

passing a $C_{5-6}$ feed stream comprising normal pentane and normal hexane to a $C_{5-6}$ HCl absorber forming a $C_{5-6}$ absorber bottoms stream comprising normal pentane, normal hexane and HCl and a $C_{5-6}$ absorber overhead stream comprising a trace amount of HCl;

passing a first hydrogen rich gas stream and a chloride feed stream containing an organic chloride compound to an organic chloride decomposition reactor containing a chloride decomposition catalyst to decompose the organic chloride compound to form a chloride effluent stream comprising hydrogen, hydrocarbon, and HCl;

passing the $C_{5-6}$ absorber bottoms stream and the chloride effluent stream to a $C_{5-6}$ isomerization reaction zone under $C_{5-6}$ isomerization conditions in the presence of a $C_{5-6}$ isomerization catalyst to convert a portion of the normal pentane and normal hexane to iso-pentane and iso-hexane, forming a $C_{5-6}$ isomerization effluent comprising normal pentane, normal hexane, iso-pentane, iso-hexane, and gases;

separating the $C_{5-6}$ isomerization effluent in a $C_{5-6}$ stabilizer column into at least a $C_{5-6}$ product stream comprising the normal pentane, normal hexane, iso-pentane, and iso-hexane, and a $C_{5-6}$ off gas stream;

passing a $C_4$ feed stream comprising normal butane to a $C_4$ HCl absorber forming a $C_4$ absorber bottoms stream comprising normal butane and HCl and a $C_4$ absorber overhead stream comprising a trace amount of HCl;

passing the $C_4$ absorber bottoms stream and a second hydrogen rich gas stream to a $C_4$ isomerization reaction zone under $C_4$ isomerization conditions in the presence of a $C_4$ isomerization catalyst to convert a portion of the normal butane to iso-butane forming a $C_4$ isomerization effluent comprising normal butane, iso-butane, and gases;

separating the $C_4$ isomerization effluent in a $C_4$ stabilizer column into at least a $C_4$ product stream comprising normal butane and iso-butane, and a $C_4$ off gas stream;

splitting the $C_{5-6}$ off gas stream into three streams, and passing the first $C_{5-6}$ off gas stream to the $C_{5-6}$ HCl absorber, passing the second $C_{5-6}$ off gas stream to the $C_4$ HCl absorber, and passing the third $C_{5-6}$ off gas stream to a chloride treater, wherein the first $C_{5-6}$ off gas stream comprises 75 to 90% of the $C_{5-6}$ off gas stream, the second $C_{5-6}$ off gas stream comprises 5 to 15% of the $C_{5-6}$ off gas stream, and the third $C_{5-6}$ off gas stream comprises 5 to 20% of the $C_{5-6}$ off gas stream;

splitting the $C_4$ off gas stream into two streams, and passing the first $C_4$ off gas stream to the $C_4$ HCl absorber, and passing the second $C_4$ off gas stream to the $C_{5-6}$ HCl absorber, wherein the first $C_4$ off gas stream comprises 75 to 95% of the $C_4$ off gas stream, and the second $C_4$ off gas stream comprises 5 to 25% of the $C_4$ off gas stream;

passing the $C_{5-6}$ absorber overhead stream from the $C_{5-6}$ HCl absorber and the $C_4$ absorber overhead stream from the $C_4$ HCl absorber to the chloride treaters;

passing the $C_{5-6}$ product stream to a deisohexanizer column; and passing the $C_4$ product stream to a deisobutanizer column.

13. The process of claim 12 further comprising:
determining an amount of HCl required in the $C_4$ absorber bottoms stream; and
controlling a flow rate of the second $C_{5-6}$ off gas stream to the $C_4$ HCl absorber based on the determined amount of HCl required in the $C_4$ HCl absorber bottoms stream.

14. The process of claim 12 wherein separating the $C_{5-6}$ isomerization effluent in the $C_{5-6}$ stabilizer column into at least the $C_{5-6}$ product stream comprising the normal pentane, normal hexane, iso-pentane, and iso-hexane, and the $C_{5-6}$ off gas stream comprises separating the $C_{5-6}$ isomerization effluent in the $C_{5-6}$ stabilizer column into at least the $C_{5-6}$ product stream comprising the normal pentane, normal hexane, iso-pentane, and iso-hexane, the $C_{5-6}$ off gas stream, and a stream comprising hydrocarbons having 3 to 4 carbon atoms.

15. The process of claim 12 further comprising at least one of:
   drying the first feed stream before passing the $C_{5-6}$ feed stream to the $C_{5-6}$ HCl absorber; or
   drying the $C_4$ feed stream before passing the $C_4$ feed stream to the $C_4$ HCl absorber.

16. The process of claim 12 wherein at least one of: the $C_{5-6}$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 0.5 to about 12 $hr^{-1}$; or the $C_4$ isomerization conditions comprise one or more of: a temperature in a range of about 80° C. to about 215° C.; a pressure in a range of about 1.4 MPa(g) to about 7.0 MPa(g); or a liquid hourly space velocity in a range of about 4 to about 24 $hr^{-1}$.

17. The process of claim 12 wherein a hydrogen to organic chloride molar ratio in the organic chloride decomposition reactor is about 350:1 to about 2700:1.

18. The process of claim 12 wherein the chloride decomposition catalyst comprises at least one of: nickel, platinum, or palladium.

19. The process of claim 12 wherein an amount of chloride equivalent in the chloride effluent stream can be calculated using an equation:

$$C*G*(1-E*F)-A*G*(1-B)*F$$

where: A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; E is a ratio of an amount of the first $C_{5-6}$ off gas stream to the total amount of the $C_{5-6}$ off gas stream; F is a fraction of HCl recovered from a combination of the first $C_{5-6}$ off gas stream and the second $C_4$ off gas stream sent to the $C_{5-6}$ HCl absorber; and G is a constant which depends on process parameters and the type of chloriding agent used.

20. The process of claim 12 wherein an amount of the second $C_{5-6}$ stream can be calculated using an equation:

$$A*(1-B*D)/C$$

where: A is a $C_4$ feed rate; B is a ratio of an amount of the first $C_4$ off gas stream sent to the $C_4$ HCl absorber to a total amount of the $C_4$ off gas stream; C is a $C_{5-6}$ feed rate; and D is a fraction of HCl recovered from a combination of the first $C_4$ off gas stream and the second $C_{5-6}$ off gas stream sent to the $C_4$ HCl absorber.

* * * * *